(12) United States Patent
Cadouri et al.

(10) Patent No.: US 9,855,090 B2
(45) Date of Patent: Jan. 2, 2018

(54) ELECTROSURGICAL SYSTEM WITH SELECTIVE CONTROL OF ACTIVE AND RETURN ELECTRODES

(71) Applicant: ArthroCare Corporation, Austin, TX (US)

(72) Inventors: Hadar Cadouri, Sunnyvale, CA (US); Philip M. Tetzlaff, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 826 days.

(21) Appl. No.: 14/158,938

(22) Filed: Jan. 20, 2014

(65) Prior Publication Data

US 2014/0135760 A1 May 15, 2014

Related U.S. Application Data

(63) Continuation of application No. 12/335,679, filed on Dec. 16, 2008, now abandoned.

(51) Int. Cl.
*A61M 3/02* (2006.01)
*A61B 18/14* (2006.01)
(Continued)

(52) U.S. Cl.
CPC ...... *A61B 18/1402* (2013.01); *A61B 18/1233* (2013.01); *A61B 18/148* (2013.01);
(Continued)

(58) Field of Classification Search
CPC .............. A61B 18/1402; A61B 18/148; A61B 18/1482; A61B 18/1485;
(Continued)

(56) References Cited

U.S. PATENT DOCUMENTS 3,952,748 A * 4/1976 Kaliher .................. A61B 18/12
219/770
5,660,567 A * 8/1997 Nierlich ............. A61B 5/14551
439/620.21
(Continued)

FOREIGN PATENT DOCUMENTS

| CN | 105266894 | 1/2016 |
| EP | 1112720 | 7/2001 |
| GB | 2518481 | 3/2015 |

*Primary Examiner* — Kevin C Sirmons
*Assistant Examiner* — Tiffany Legette-Thompson
(74) *Attorney, Agent, or Firm* — David A. Warmbold

(57) ABSTRACT

Electrosurgical system with selective control of active and return electrodes. At least some of the illustrative embodiments are systems comprising an electrosurgical wand and an electrosurgical controller. The wand comprises a non-conductive outer surface, at least three electrodes disposed on a distal end of the wand, and at least three electrical leads extending from a proximal end of the wand (one electrical lead electrically coupled to each electrode). The controller comprises a voltage generator and a control circuit coupled between the voltage generator and the electrodes of the wand. The control circuit is configured to: selectively electrically couple the active terminal singly and in combination to the electrodes of the wand; and selectively electrically couple the return terminal singly and in combination to electrodes of the wand.

17 Claims, 5 Drawing Sheets

(51) Int. Cl.
*A61B 18/16* (2006.01)
*A61B 18/12* (2006.01)
*A61B 18/00* (2006.01)

(52) U.S. Cl.
CPC .......... *A61B 18/16* (2013.01); *A61B 18/1206* (2013.01); *A61B 2018/00345* (2013.01); *A61B 2018/00404* (2013.01); *A61B 2018/00577* (2013.01); *A61B 2018/00619* (2013.01); *A61B 2018/124* (2013.01); *A61B 2018/1467* (2013.01); *A61B 2018/1472* (2013.01); *A61B 2218/002* (2013.01)

(58) Field of Classification Search
CPC .... A61B 2018/1472; A61B 2018/1467; A61B 2018/00577; A61B 2018/00404; A61B 2018/00345; A61B 18/16; A61B 18/1233; A61B 18/1206; A61B 2018/00619; A61B 2018/124; A61B 2218/002
USPC .......................................................... 604/41
See application file for complete search history.

(56) References Cited

U.S. PATENT DOCUMENTS

| | | |
|---|---|---|
| 5,951,545 A | 9/1999 | Schilling et al. |
| 6,786,906 B1 | 9/2004 | Cobb |
| 2004/0054366 A1* | 3/2004 | Davison ............... A61B 18/042 606/39 |
| 2005/0131402 A1* | 6/2005 | Ciarrocca .......... A61B 18/1402 606/41 |
| 2006/0015095 A1 | 1/2006 | Desinger et al. |
| 2007/0203482 A1 | 8/2007 | Ein-Gal |
| 2008/0140069 A1* | 6/2008 | Filloux ............... A61B 18/1492 606/41 |
| 2008/0183251 A1 | 7/2008 | Azar et al. |
| 2008/0249523 A1* | 10/2008 | McPherson ........ A61B 18/1445 606/41 |
| 2008/0294156 A1 | 11/2008 | Newton et al. |
| 2011/0118731 A1 | 5/2011 | Ladtkow |
| 2012/0083779 A1 | 4/2012 | Hosier |
| 2014/0081256 A1 | 3/2014 | Carmel et al. |
| 2015/0196350 A1 | 7/2015 | Carmel et al. |
| 2015/0282857 A1 | 10/2015 | Anderson et al. |

* cited by examiner

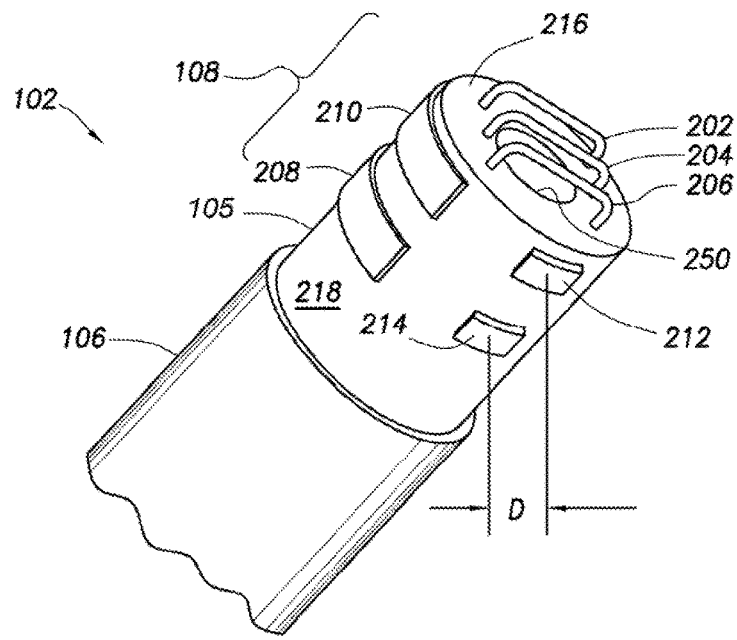
FIG.2
FIG.4
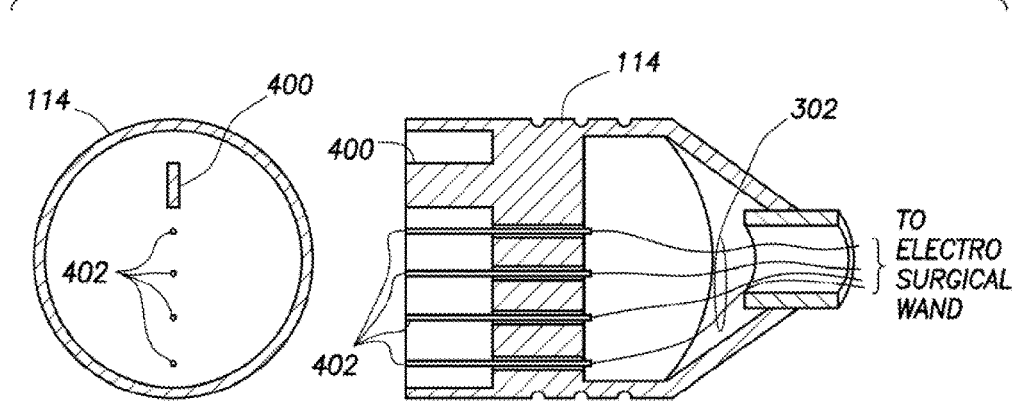

ELECTROSURGICAL SYSTEM WITH SELECTIVE CONTROL OF ACTIVE AND RETURN ELECTRODES

CROSS-REFERENCE TO RELATED APPLICATIONS

This application is a continuation of U.S. patent application Ser. No. 12/335,679 filed Dec. 16, 2008, the complete disclosures of which are incorporated herein by reference for all purposes.

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue, or meniscus, cartilage and/or sinovial tissue in a joint. In a coagulation mode, the electrosurgical device may aid the surgeon in reducing internal bleeding by assisting in the coagulation and/or sealing of vessels.

However, while the mode of operation of an electrosurgical system is controlled to some extent by the voltage applied to the electrodes of an electrosurgical wand, the physical size and placement of electrodes on the electrosurgical wand also affect operation. For example, in an ablation mode, a relatively small active electrode conducting current to a proximally-located larger return electrode may be preferred to very precisely control the tissue ablated. By contrast, in a coagulation mode, relatively large active and return electrodes, perhaps along the side of an electrosurgical wand and yet still proximate to the distal end, may be preferred to ensure larger surface area for coagulation.

In some situations, a surgeon may choose to change electrosurgical wands as between, for example, an ablation of tissue and a coagulation procedure. In other situations, an electrosurgical system may have the ability to change between an ablation and coagulation mode by controlling the active electrode on the electrosurgical wand and/or the voltage output of the controller. However, any advance that increases the functionality of an electrosurgical system provides competitive advantage.

BRIEF DESCRIPTION OF THE DRAWINGS

For a detailed description of exemplary embodiments of the invention, reference will now be made to the accompanying drawings in which:

FIG. 2 shows a perspective view a portion of a wand in accordance with at least some embodiments;

FIG. 4 shows both an elevational end-view (left) and a cross-sectional view (right) of a wand connector in accordance with at least some embodiments;

NOTATION AND NOMENCLATURE

Figure 1:
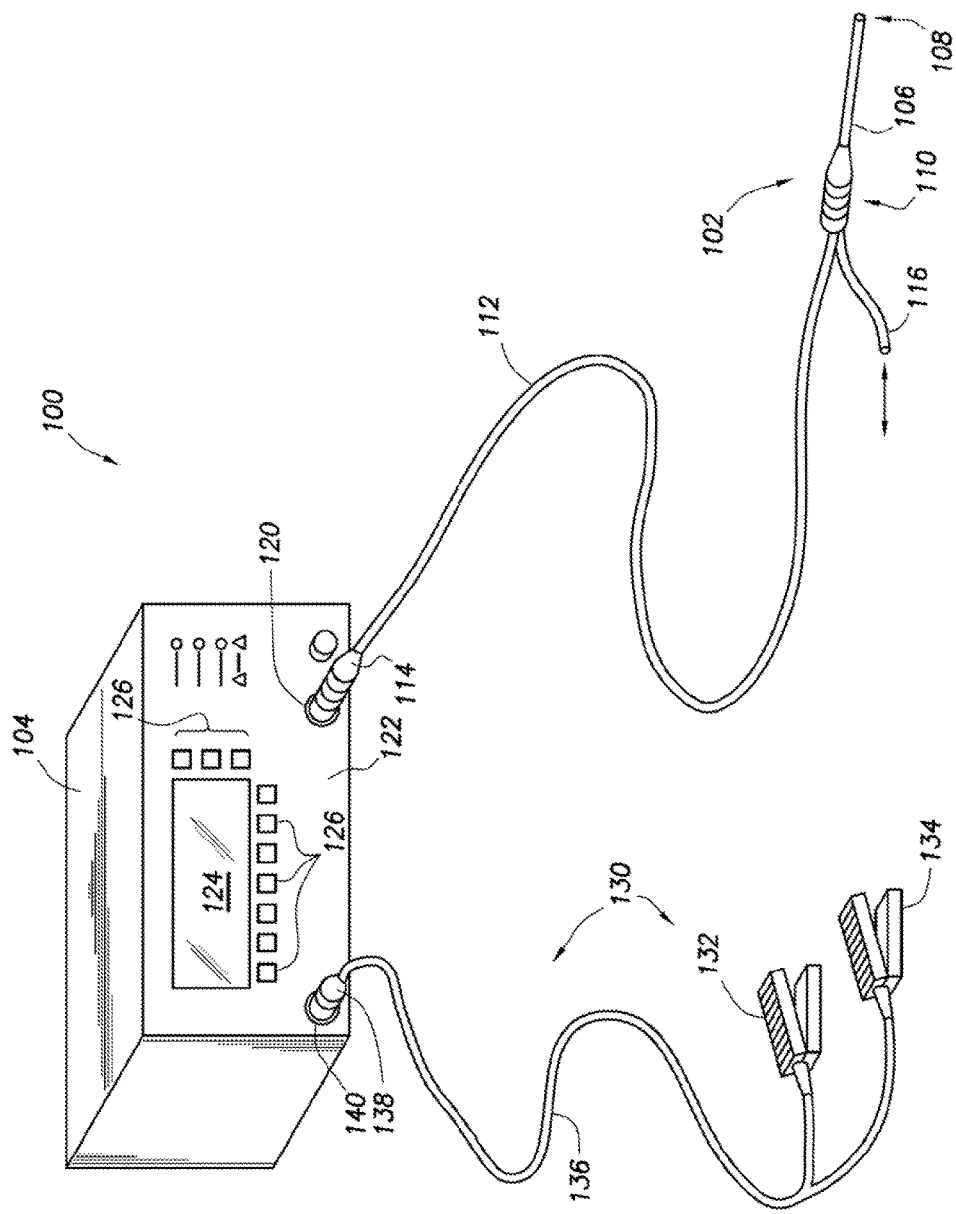
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator, power generator, or other suitable energy source.

"Return electrode" shall mean an electrode of an electrosurgical wand which serves to provide a current flow path for electrons with respect to an active electrode, and/or an electrode of an electrical surgical wand which may not itself produce an electrically-induced tissue-altering effect on tissue targeted for treatment.

"Proximate" shall mean, in relation to spacing of electrodes on a wand, within 5 centimeters, and in some cases less than 1 centimeter.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical instrument 102 (hereinafter "wand") coupled to an electrosurgical controller 104 (hereinafter "controller"). The wand 102 comprises an elongate shaft 106 that includes distal end 108 where at least some electrodes are disposed. In certain embodiments, the elongate shaft 106 comprises a conductive material, but is covered with an insulating material. The elongate shaft 106 further defines a handle or proximal end 110, where a user may grip the wand 102 during a surgical procedure. The wand 102 further comprises a flexible multi-conductor cable 112 housing a plurality of electrical leads (not specifically shown in FIG. 1), and the flexible multi-conductor cable 112 terminates in a wand connector 114. Though not expressly shown in the FIG. 1, in some embodiments wand 102 may include an internal passage or lumen fluidly coupled to a flexible tubular member 116. The internal passage and flexible tubular member 116 may be used as a conduit to supply conductive fluid, a non-conductive irrigant, or other desired fluid to be proximate to the distal end 108, or the internal passage and flexible tubular member may be used to aspirate the area proximate to the distal end 108 of the wand 102.

As shown in FIG. 1, the wand 102 couples to the controller 104, such as by a controller connector 120, on an outer surface 122 (in the illustrative case of FIG. 1 the front surface). A display device or interface panel 124 is visible through the outer surface 122, and in some embodiments a user may select operational modes of the controller 104 by way of the interface device 124 and related buttons 126. The interaction of the interface device 124 and buttons 126 is discussed more thoroughly below with respect to FIG. 5.

Still referring to FIG. 1, in some embodiments the electrosurgical system 100 may also comprise a foot pedal assembly 130. The foot pedal assembly 130 may comprise one or more pedal devices 132 and 134, a flexible multi-conductor cable 136 and a pedal connector 138. While only two pedal devices 132, 134 are shown, any number of pedal devices may be implemented. The outer surface 122 of the controller 104 may comprise a corresponding connector 140 that couples to the connector 138. A physician may use the foot pedal assembly 130 to control various aspects of the controller 104, such as the operational mode. For example, a pedal device, such as pedal device 132, may be used for on-off control of the application of radio frequency (RF) energy to the wand 102, and more specifically for control of energy in an ablation mode. A second pedal device, such as pedal device 134, may be used to control and/or set the operational mode of the electrosurgical system. For example, actuation of pedal device 134 may switch between ablation mode and a coagulation mode. Alternatively, pedal device 134 may be used to control the application of RF energy to wand 102 in a coagulation mode. The pedal devices may also be used to change the voltage level delivered to wand 102. As another example, actuation of the pedal device 134 may change the configuration of active and return electrodes on the wand 102.

The electrosurgical system 100 of the various embodiments may have a variety of operational modes. One such mode employs Coblation® technology. In particular, the assignee of the present disclosure is the owner of Coblation® technology. Coblation® technology involves the application of a RF signal between one or more active electrodes and one or more return electrodes of the wand 102 to develop high electric field intensities within conductive fluid in the vicinity of the target tissue sufficient to volumetrically dissociate or otherwise ablate tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

In addition to the Coblation® mode, the electrosurgical system 100 of FIG. 1 is also useful for sealing larger arterial vessels (e.g., on the order of about 1 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 has a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032, 6,149,120 and 6,296,136, the complete disclosures of which are incorporated herein by reference.

FIG. 2 illustrates the distal end 108 of wand 102. In some embodiments, distal end 108 of wand 102 comprises electrode support member 105 that may be constructed of an inorganic insulating (i.e., non-conductive) material. The distal end 108 further comprises a plurality of electrodes. For example, in the illustrative case of FIG. 2, seven electrodes 202, 204, 206, 208, 210, 212 and 214 are shown; however, any suitable configuration of three or more electrodes may be equivalently used. As illustrated in FIG. 2, the electrodes may take many forms. Electrodes 202, 204 and 206 are illustrative of wire-type electrodes that protrude slightly from the end 216 of electrode support member 105. The wire-type electrodes 202, 204 and 206 may be used, for example, singly or in combination to be the active electrodes to which the RF energy is applied in the ablation mode. Electrodes 208, 210 are disposed on a radial or side surface 218 of the distal end 108, and the electrodes 208, 210 span a certain circumferential distance. Electrodes 212, 214 are similar to electrodes 208, 210, but span a smaller circumferential distance. The electrodes 208, 210, 212 and 214 may be used in some modes as return electrodes for ablation, and in other modes may be the active and/or return electrodes in the coagulation mode. Other electrode types, such as button electrodes (i.e., round electrodes), arrays of button electrodes, or screen electrodes, may be equivalently used. Alternatively, the disposition of electrodes may also be changed such that smaller electrodes are disposed on a side surface and not on an end of wand 102.

Still referring to FIG. 2, in some embodiments the wand 102 includes an internal lumen 250 that fluidly couples to the flexible tubular member 116 (FIG. 1). In some modes of operation, the internal lumen 250 may preferably be used to supply conductive fluid to the target area. In other modes of operation, the internal lumen 250 may be used to aspirate the area near the distal end 108 of the wand 102, such as when sufficient conductive fluid is already present at the target location and ablation is taking place, or to remove byproducts of the ablation process including fluid, gas bubbles, or particles of tissue.

In accordance with the various embodiments, while a wand 102 may be designed to have a multitude of electrode types and arrangements, in at least some embodiments the electrodes are in a fixed relationship for any one design. For example, the center-to-center distance "D" of illustrative electrodes 212 and 214 is set by the design of the particular wand 102, and remains constant as between use and non-use. Similar fixed relationships exist between all the illustrative electrodes of wand 102. Furthermore, while a wand 102 may be designed to have a multitude of exposed electrode surface areas, in at least some embodiments at least one electrode has a surface area less than three-quarters the surface area of another electrode. In the illustrative case of FIG. 2, for example, electrode 212 as shown has a surface area less than three-quarters of either electrode 208 or 210. Thus, in accordance with the various embodiments, one is able not only to select particular electrodes to control the relationship of the electrodes from a distance perspective, but is also able to select electrodes to control the relative cumulative proportion of surface area between the active electrodes and the return electrodes. For example, in a first mode, a user may select an active electrode and a return electrode having the same surface area (e.g., electrodes 208 and 210); however, in a second mode the user may select an active electrode and a return electrode having different sizes (e.g., electrode 212 as an active electrode and electrode 210 as a return electrode).

In at least some embodiments, in ablation modes (using, for example, Coblation® technology as discussed herein) the one or more return electrodes are spaced proximally from the one or more active electrodes a suitable distance to avoid electrical shorting between the electrodes when in the presence of electrically conductive fluid. In many cases, the distal edge of the exposed surface of the closest return electrode is between about 0.5 milli-meters (mm) to about 25 mm from the proximal edge of the exposed surface of the closest active electrode, and in some embodiments between about 1.0 mm to 5.0 mm. For example, electrode 208 may be selected to be a return electrode and electrode 210 may be selected to be an active electrode, and the axial distance between electrode 208 and 210 may be in the range of 0.5 mm to 25 mm. As yet another example using the Coblation® technology, one, two or all the wire-type electrodes 202, 204 and 206 may be active, and electrode 210 (which was the active electrode in the previous example) may be the return electrode. In the second example, the axial distance between the active electrode(s) and the return electrode 210 may be 0.5 mm to 25 mm. As yet another example, electrodes 202 and 206 may be return electrodes, with any of the electrodes 204, 208, or 210 being active. The distances may vary with different voltage ranges, conductive fluids, and proximity of tissue structures to available active and return electrodes. In some embodiments, return electrode may have an exposed length in the range of about 1 mm to 20 mm.

As alluded to by the examples of preceding paragraph, in accordance with at least some embodiments, any single electrode or combination of multiple electrodes may be selected as the active electrode for a particular mode of operation. Likewise in accordance with at least some embodiments, any single electrode or combination of multiple electrodes may be selected as the return electrode for a particular mode of operation. However, in any scenario discussed above, at least one electrode shall be selected as an active electrode and at least one electrode shall be selected as a return electrode. It follows that, in accordance with various embodiments, most if not all electrodes of wand 102 are preferably electrically isolated from each other, and thus have individual electrical leads that run from each electrode to the wand connector 114.

Figure 3:
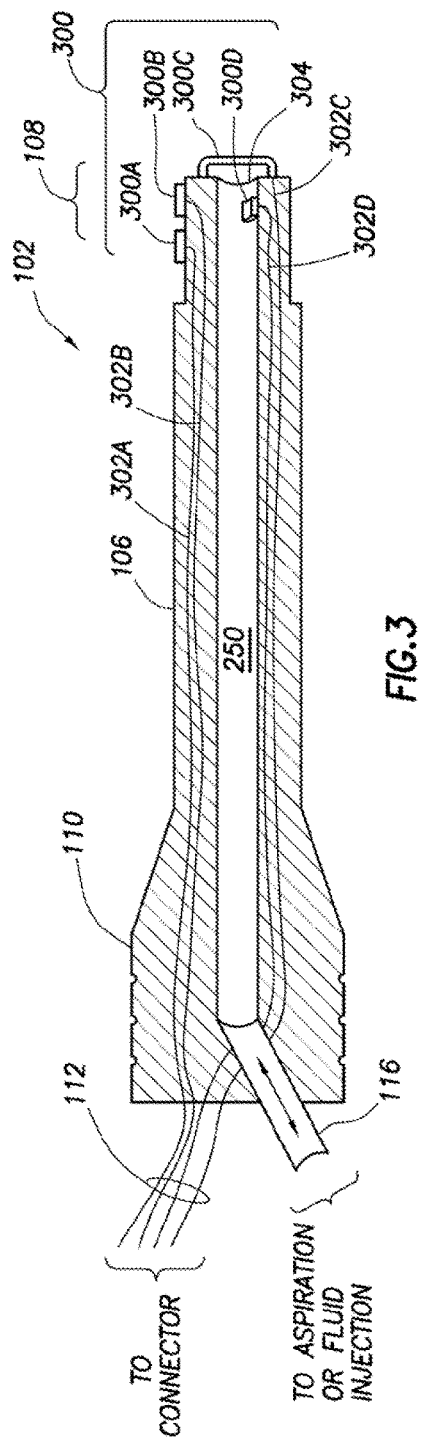
FIG. 3 shows a cross-sectional view of a wand in accordance with at least some embodiments.

FIG. 3 shows a cross-sectional view of wand 102 in accordance with at least some embodiments. In particular, FIG. 2 illustrates the elongate shaft 106 comprising distal end 108 and proximal end 110. Distal end 108 comprises a plurality of electrodes 300, and while the electrodes 300 are similar to the electrodes of FIG. 2, electrodes 300 are not necessarily the same as those of FIG. 2. In accordance with the various embodiments where any electrode 300 may be selected singly or in combination with other electrodes to be active electrode(s), and likewise any electrode 300 may be selected singly or in combination with other electrodes 300 to be the return electrode(s), each electrode 300 has an electrical lead associated therewith that runs through the elongate shaft 106 to the flexible multi-conductor cable 112. In particular, electrode 300A has dedicated electrical lead 302A which runs within the elongate shaft to the become part of cable 112. Similarly, electrode 300B has dedicated electrical lead 302B which runs within the elongate shaft 106 to become part of cable 112. Illustrative electrodes 300C and 300D likewise have dedicated electrical leads 302C and 302D which run within the elongate shaft 106 to become part of cable 112. In some embodiments, the elongate shaft 106 has dedicated internal passages (in addition to internal lumen 250) through which the electrical leads 302 run. In other embodiments, the electrical leads 302 may be cast within the material that makes up the elongate shaft.

FIG. 3 also illustrates internal lumen 250 having an aperture 304 fluidly coupled to the flexible tubular member 116 on the proximal end 110. In other embodiments, the fluid coupling of the internal lumen 250 to the flexible tubular member 116 may be between the distal end 108 and proximal end 110. The internal lumen 250 is used in some embodiments to supply conductive fluid through the aperture 302 to the target area, and in other embodiments the internal lumen 250 is used for aspiration of ablated tissue fragments and/or molecules. In some embodiments, an electrode 300D may be disposed within the internal lumen 250 proximate to the aperture 304. An electrode 300D within the internal lumen 250 may, for example, be selected as either an active or return electrode in an ablation mode, and may aid in disassociation of tissue pieces into smaller pieces during ablation and aspiration procedures.

The power provided to the wand 102 may be current limited or otherwise controlled so that undesired heating of the target tissue or surrounding (non-target) tissue does not occur. In some embodiments, current limiting inductors are placed in series with some or all the electrodes, where the inductance of each inductor is in the range of 10 micro-Henries (pH) to 50,000 pH, depending on the electrical properties of the target tissue, the desired tissue heating rate and the operating frequency. Alternatively, inductor-capacitor (LC) circuit structures may be employed, as described in U.S. Pat. No. 5,697,909, the complete disclosure of which is incorporated herein by reference. Additionally, current-limiting resistors may be selected. The current-limiting resistors will have a large positive temperature coefficient of resistance so that, as the current level begins to rise for any individual active electrode in contact with a low resistance medium (e.g., saline or blood), the resistance of the current limiting resistor increases significantly, thereby reducing the power delivery from the active electrode into the low resistance medium. In some embodiments, the current limited devices may reside within the elongate shaft 106, or may reside within the flexible cable 112.

As illustrated in FIG. 1, flexible multi-conductor cable 112 (and more particularly its constituent electrical leads 302) couple to the wand connector 114. Wand connector 114 couples to the controller 104, and more particularly the controller connector 120. FIG. 4 shows both a cross-sectional view (right) and an end elevation view (left) of wand connector 114 in accordance with at least some embodiments. In particular, wand connector 114 comprises a tab 400. Tab 400 works in conjunction with a slot on controller connector 120 (shown in FIG. 5) to ensure that the wand connector 114 and controller connector 120 only couple in one relative orientation. The illustrative wand connector 114 further comprises a plurality of electrical pins 402 protruding from wand connector 114. The electrical pins 402 are coupled one each to a single electrical lead 302. Stated otherwise, each electrical pin 402 couples to a single electrical lead 302, and thus each illustrative electrical pin 402 couples to a single electrode 300 (FIG. 3). While FIG. 4 shows only four illustrative electrical pins, in some embodiments up to 26 or more electrical pins may be present in the wand connector 114.

Figure 5:
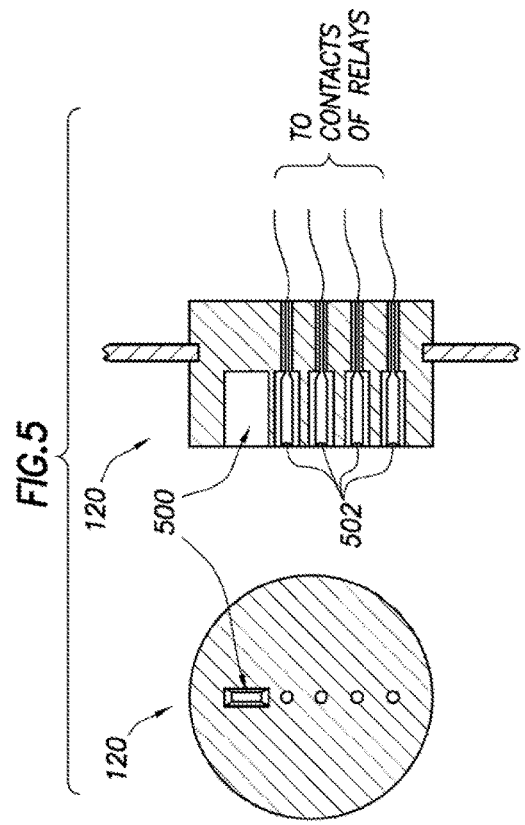
FIG. 5 shows both an elevational end-view (left) and a cross-sectional view (right) of a controller connector in accordance with at least some embodiments.

FIG. 5 shows both a cross-sectional view (right) and an end elevation view (left) of controller connector 120 in accordance with at least some embodiments. In particular, controller connector 120 comprises a slot 500. Slot 500 works in conjunction with a tab 400 on wand connector 114 (shown in FIG. 4) to ensure that the wand connector 114 and controller connector 120 only couple in one orientation. The illustrative controller connector 120 further comprises a plurality of electrical pins 502 residing with respective holes of controller connector 120. The electrical pins 502 are each individually coupled to a relay within the controller 104 (discussed more thoroughly below). When wand connector 114 and controller connector 120 are coupled, each electrical pin 502 couples to a single electrical pin 402, and thus each illustrative electrical pin 502 couples to a single electrode 300 (FIG. 3). While FIG. 5 shows only four illustrative electrical pins, in some embodiments as many as 26 or more electrical pins may be present in the wand connector 120.

While illustrative wand connector 114 is shown to have the tab 400 and male electrical pins 402, and controller connector 120 is shown to have the slot 500 and female electrical pins 502, in alternative embodiments the wand connector has the female electrical pins and slot, and the controller connector 120 has the tab and male electrical pins. In other embodiments, the arrangement of the pins within the connectors may enable only a single orientation for connection of the connectors, and thus the tab and slot arrangement may be omitted. In yet still other embodiments, other suitable mechanical arrangements to ensure the wand connector and controller connector couple in only one orientation may be equivalently used.

Figure 6:
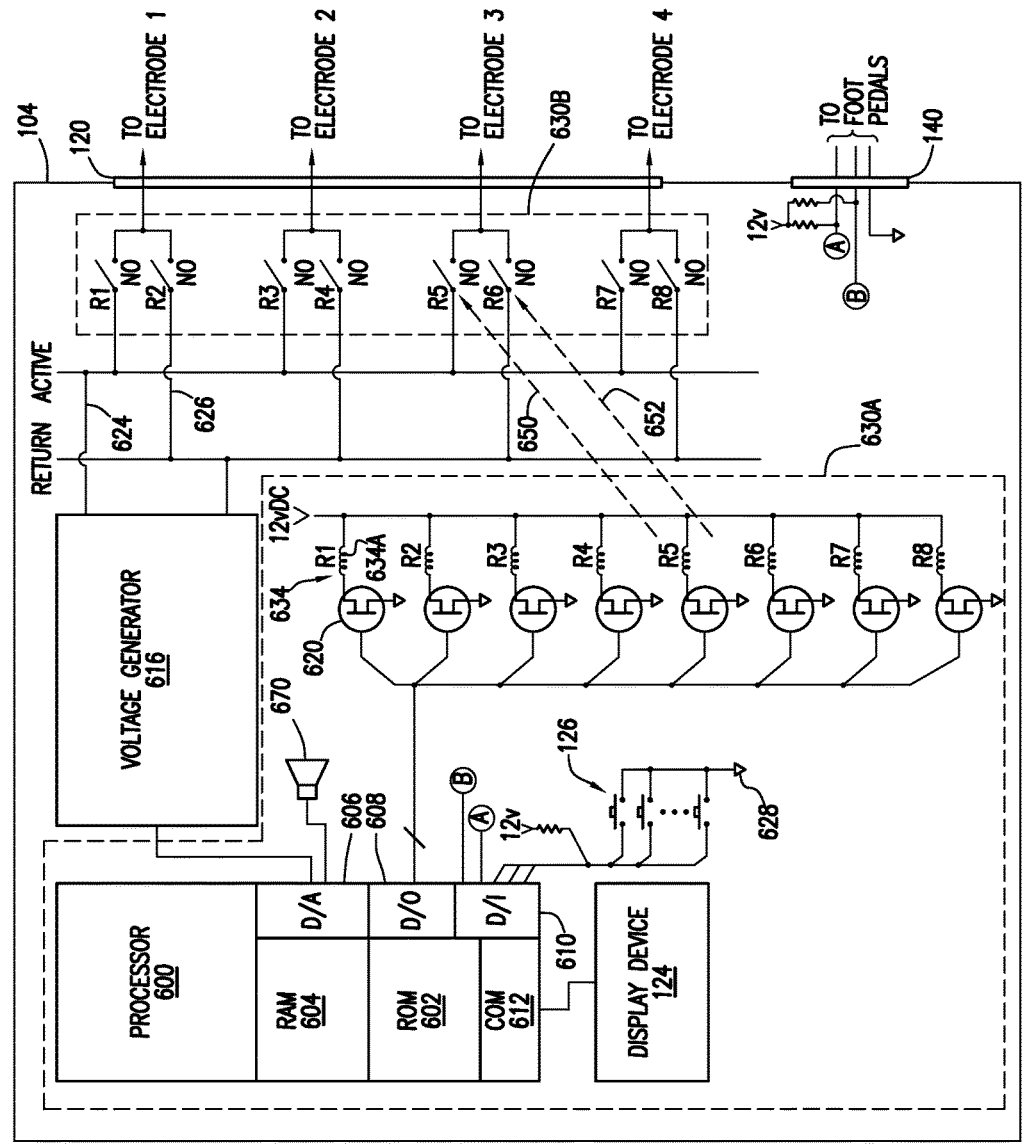
FIG. 6 shows an electrical block diagram of an electrosurgical controller in accordance with at least some embodiments.

FIG. 6 illustrates a controller 104 in accordance with at least some embodiments. In particular, the controller 104 in accordance with at least some embodiments comprises a processor 600. The processor 600 may be a microcontroller, and therefore the microcontroller may be integral with read-only memory (ROM) 602, random access memory (RAM) 604, digital-to-analog converter (D/A) 606, digital outputs (D/O) and digital inputs (D/I) 610. The processor 600 may further provide one or more externally available peripheral busses, such as a serial bus (e.g., $I^2C$), parallel bus, or other bus and corresponding communication mode. The processor 600 may further be integral with a communication logic 612 to enable the processor 600 to communicate with external devices, as well as internal devices, such as display device 124. Although in some embodiments the controller 104 may implement a microcontroller, in yet other embodiments the processor 600 may be implemented as a standalone central processing unit in combination with individual RAM, ROM, communication, D/A, D/O and D/I devices, as well as communication port hardware for communication to peripheral components.

ROM 602 stores instructions executable by the processor 600. In particular, the ROM 602 may comprise a software code that implements the various embodiments of selectively coupling the electrodes of the wand to the voltage generator 616, as well as interfacing with the user by way of the display device 614 and/or the foot pedal assembly 130 (FIG. 1) and/or a speaker assembly (not specifically shown). The RAM 604 may be the working memory for the processor 600, where data may be temporarily stored and from which instructions may be executed. Processor 600 couples to other devices within the controller 104 by way of the D/A converter 606 (i.e., the voltage generator 616), digital outputs 608 (i.e., electrically controlled switches 620), digital inputs 610 (i.e., push button switches 126, and the foot pedal assembly 130 (FIG. 1)), communication device 612 (i.e., display device 124), and other peripheral devices. The other peripheral devices may comprise electrode relays and/or switches, devices to set desired voltage generator 616 output voltage, and other secondary devices internal to the generator.

Voltage generator 616 generates selectable alternating current (AC) voltages that are applied to the electrodes of the wand 102. In some embodiments, the voltage generator defines an active terminal 624 and a return terminal 626. The active terminal 624 is the terminal upon which the voltages and electrical currents are induced by the voltage generator 616, and the return terminal 626 provides a return path for electrical currents. In some embodiments, the return terminal 626 may provide a common or ground being the same as the common or ground within the balance of the controller 104 (e.g., the common 628 used on push-buttons 622), but in other embodiments the voltage generator 616 may be electrically "floated" from the balance of the supply power in the controller 104, and thus the return terminal 626, when measured with respect to the common (e.g., common 628) within the controller 104, may show a voltage difference; however, an electrically floated voltage generator 616 and thus the potential for voltage readings on the return terminal 626 does not negate the return terminal status of the terminal 626 relative to the active terminal 624.

The voltage generated and applied between the active terminal 624 and return terminal 626 by the voltage generator 616 is a RF signal that, in some embodiments, has a frequency of between about 5 kilo-Hertz (kHz) and 20 Mega-Hertz (MHz), in some cases being between about 30 kHz and 2.5 MHz, preferably being between about 50 kHz and 500 kHz, often less than 350 kHz, and often between about 100 kHz and 200 kHz. In some applications, a frequency of about 100 kHz is useful because target tissue impedance is much greater at 100 kHz. In other applications, such as procedures in or around the heart or head and neck, higher frequencies may be desirable (e.g., 400-600 kHz) to reduce low frequency current flow into the heart or the nerves of the head and neck.

The RMS (root mean square) voltage generated by the voltage generator 616 may be in the range from about 5 Volts (V) to 1000 V, preferably being in the range from about 10 V to 500 V, often between about 10 V to 400 V depending on the active electrode size, the operating frequency and the operation mode of the particular procedure or desired effect on the tissue (i.e., contraction, coagulation, cutting or ablation). The peak-to-peak voltage generated by the voltage generator 616 for ablation or cutting in some embodiments is a square wave form in the range of 10 V to 2000 V and in some cases in the range of 100 V to 1800 V and in other cases in the range of about 28 V to 1200 V, often in the range of about 100 V to 320V peak-to-peak (again, depending on the electrode size, number of electrodes the operating frequency and the operation mode). Lower peak-to-peak voltage is used for tissue coagulation, thermal heating of tissue, or collagen contraction and may be in the range from 50 V to 1500V, preferably 100 V to 1000 V and more preferably 60 V to 130 V peak-to-peak (again, these values are computed using a square wave form).

The voltage and current generated by the voltage generator 616 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of the square wave voltage produced by the voltage generator 616 is on the order of about 50% for some embodiments as compared with pulsed lasers which may have a duty cycle of about 0.0001%. Although square waves are generated and provided in some embodiments, the various embodiments may be equivalently implemented with many applied voltage waveforms (e.g., sinusoidal, triangular).

Still referring to the voltage generator 616, the voltage generator 616 delivers average power levels ranging from several milliwatts to hundreds of watts per electrode, depending on the voltage applied to the target electrode for the target tissue being treated, and/or the maximum allowed temperature selected for the wand 102. The voltage generator 616 is configured to enable a user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the voltage generator 616 may have a filter that filters leakage voltages at frequencies below 100 kHz, particularly voltages around 60 kHz. Alternatively, a voltage generator 616 configured for higher operating frequencies (e.g., 300 kHz to 600 kHz) may be used in certain procedures in which stray low frequency currents may be problematic. A description of one suitable voltage generator 616 can be found in commonly assigned U.S. Pat. Nos. 6,142,992 and 6,235,020, the complete disclosure of both patents are incorporated herein by reference for all purposes.

In accordance with at least some embodiments, the voltage generator 616 is configured to limit or interrupt current flow when low resistivity material (e.g., blood, saline or electrically conductive gel) causes a lower impedance path between the return electrode(s) and the active electrode(s). Further still, in some embodiments the voltage generator 616 is configured by the user to be a constant current source (i.e., the output voltage changes as function of the impedance encountered at the wand 102).

In some embodiments, the various operational modes of the voltage generator 616 may be controlled by way of digital-to-analog converter 606. That is, for example, the processor 600 may control the output voltage by providing a variable voltage to the voltage generator 616, where the voltage provided is proportional to the voltage generated by the voltage generator 616. In other embodiments, the processor 600 may communicate with the voltage generator by way of one or more digital output signals from the digital output 608 device, or by way of packet based communications using the communication 612 device (the alternative embodiments not specifically shown so as not to unduly complicate FIG. 6).

In addition to controlling the output of the voltage generator 616, in accordance with the various embodiments the controller 104 is also configured to selectively electrically couple the active terminal 624 singly or in combination to the electrodes of the wand (by way of the electrical pins of the controller connector 120). Likewise, in the various embodiments, the controller 104 is also configured to selectively electrically couple the return terminal 626 singly or in combination to the electrodes of the wand (again by way of the electrical pins of the controller connector 120). In order to perform the selective coupling, the controller 104 implements a control circuit 630, shown in dashed lines in FIG. 6. For convenience of the figure the control circuit has two parts, 630A and 630B, but the two parts nevertheless comprise the control circuit 630. In particular, the control circuit 630 comprises the processor 600, voltage controlled switches 620 and mechanical relays R1-R6. The coils of relays R1-R6 are shown within portion 630A, while the contacts for each mechanical relay are shown within portion 630B. The correlation between the coils for mechanical relays R5 and R6 and the contacts for mechanical relays R5 and R6 are shown by dashed arrow-headed lines 650 and 652 respectively. The correlation between the remaining coils and contacts is not specifically shown with arrow-headed lines so as not to unduly complicate the figure; however, the correlation is noted by way of corresponding references.

In accordance with at least some embodiments, at least three electrodes of the wand 102 are separately electrically coupled to the controller 104. Thus, the description of FIG. 6 is based on three separately electrically coupled electrodes, but it will be understood that three or more separately electrically coupled electrodes may be used. The electrical pin of the controller connector 120 for each electrode is configured to be selectively coupled to either the active terminal 624 or the return terminal 626. For example, the electrical lead configured to couple illustrative electrode 1 of FIG. 6 couples to the normally open contact terminals for the mechanical relays R1 and R2. The other side of the normally open contact for mechanical relay R1 couples to the active terminal 624, while the other side of the normally open contact for the mechanical relay R2 couples to the return terminal 626. Thus, by selectively activating mechanical relay R1 or mechanical relay R2, electrode 1 can be either an active or return electrode in the surgical procedure. Alternatively, both relays can remain inactivated, and thus electrode 1 may remain unconnected.

Similarly, the electrical lead configured to couple illustrative electrode 2 couples to the normally open contact terminals for the mechanical relays R3 and R4. The other side of the normally open contact for mechanical relay R3 couples to the active terminal 624, while the other side of the normally open contact for the mechanical relay R4 couples to the return terminal 626. Thus, by selectively activating mechanical relay R3 or mechanical relay R4, electrode 2 can be either an active or return electrode in the surgical procedure. Alternatively, both relays R3 and R4 can remain inactivated, and thus electrode 2 may remain unconnected. Finally with respect to the illustrative electrode 3, the electrical lead configured to couple to illustrative electrode 3 couples to the normally open contact terminals for the mechanical relays R5 and R6. The other side of the normally open contact for mechanical relay R5 couples to the active terminal 624, while the opposite side of the normally open contact for the mechanical relay R6 couples to the return terminal 626. Thus, by selectively activating mechanical relay R5 or mechanical relay R6, electrode 3 can be either an active or return electrode in the surgical procedure. Alternatively, both relays can remain inactivated, and thus electrode 3 may remain unconnected.

In accordance with at least some embodiments, mechanical relays R1-R6 are selectively activated (by way of their respective coils 634) by voltage controlled switches 620. For example, when the control circuit 630 desires to couple the active terminal to electrode 1, the voltage controlled switch 620A is activated, which allows current to flow through the coil 634A of mechanical relay R1. Current flow through the coil 634 activates the relay, thus closing (making conductive) the normally open contacts. Similarly, the control circuit 630 may selectively activate any of the voltage controlled switches 620, which in turn activate respective mechanical relays R1-R6. In accordance with at least some embodiments, each mechanical relay is a part number JW1FSN-DC 12V relay available from Panasonic Corporation of Secaucus, N.J.; however, other mechanical relays may be equivalently used. Moreover, while FIG. 6 illustrates the use of field effect transistors as the voltage controlled switches 620 to control the current flow through coils of the mechanical relays, other devices (e.g., transistors, or if coils use AC driving current, triacs) may be equivalently used. Further still, in embodiments where the digital outputs 608 have sufficient current carrying capability, the voltage controlled switches may be omitted.

The selection of which electrode(s) of the wand 102 be active electrodes, and which electrode(s) to be return electrodes, may be determined in any of several forms. For example, a user may observe options for electrode selection by way of the display device 124, and may select particular options by interaction with the controller 104 by way of push buttons 126. In other embodiments, selection of particular electrodes as active or return may be made way of foot pedal assembly 102. In the embodiments illustrated in FIG. 6, selection of particular electrodes as active or return is conveyed to the illustrative processor 600 by way of the digit inputs 610; however, FIG. 6 is merely illustrative of a control circuit 630 implemented using a processor. In other embodiments, the processor may be omitted and the logic implemented by way of discrete logic devices.

In order to illustrate the flexibility of the electrosurgical system in accordance with the various embodiments, the table below shows the possible status of each electrode in a system having an illustrative three electrodes:

TABLE (1)

| Electrode 1 | Electrode 2 | Electrode 3 |
|---|---|---|
| Isolated | Isolated | Isolated |
| Return | Active | Active |
| Return | Return | Active |
| Active | Return | Return |
| Active | Active | Return |
| Active | Isolated | Return |
| Return | Isolated | Active |
| Isolated | Active | Return |
| Isolated | Return | Active |
| Active | Return | Isolated |
| Return | Active | Isolated |

Where "Isolated" indicates that a particular electrode is connected to neither the active terminal nor the return terminal of the voltage generator, "Active" means that the electrode is connected to the active terminal of the voltage generator, and "Return" means that the electrode is coupled to the return terminal of the voltage generator. It should be noted that in certain configurations an "isolated" electrode may still attract current and may heat up, acting essentially as an antennae. In this scenario, the isolated state may be referred to as "floating." Table (1) illustrates that, in accordance with at least some embodiments, an electrode of the wand can be an active electrode or a return electrode, and that depending on the mode of operation, multiple electrodes may be the active electrode at any one time. Likewise, multiple electrodes may be a return electrode at any one time.

Figure 7:
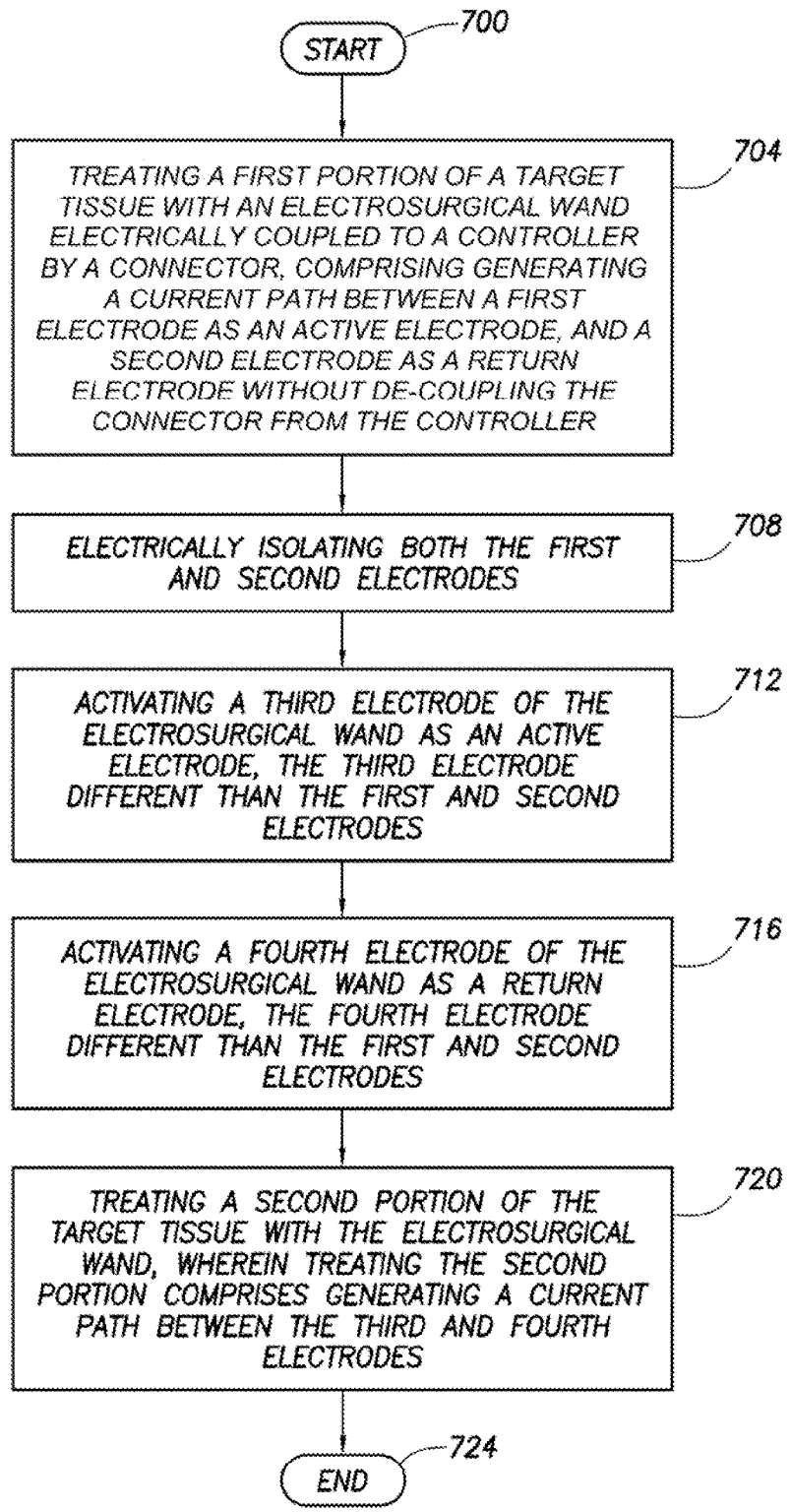
FIG. 7 shows a method in accordance with at least some embodiments.

FIG. 7 illustrates a method in accordance with at least some embodiments. In particular, the method starts (block 700) and proceeds to treating a first portion of a target tissue with an electrosurgical wand electrically coupled to a controller by a connector by generating a current path between a first electrode of the wand as an active electrode, and a second electrode of the wand as a return electrode (block 704), for example, during a molecular disassociation. Then, and without de-coupling the connector from the controller, the method proceeds to electrically isolating both the first and second electrodes (block 708), activating a third electrode of the electrosurgical wand as an as an active electrode with the third electrode different than the first and second electrodes (block 712), and activating a fourth electrode of the electrosurgical wand as a return electrode with the fourth electrode different than the first and second electrodes (block 716). Thereafter, the method comprises treating a second portion of the target tissue with the electrosurgical wand (block 720), and the method ends (block 724). Treating the second portion of the target tissue may comprise, for example, generating a current path between the third and fourth electrodes during a molecular disassociation The above discussion is meant to be illustrative of the principles and various embodiments of the present invention. Numerous variations and modifications possible. For example, while three or more electrodes may have the ability to be either active, return or isolated, other electrodes may be present without departing from the scope and spirit of the invention. Moreover, two electrodes may be electrically coupled within the wand 102, such that the coupled electrodes act as single electrode from the perspective of the controller, with the ability to be active, return or isolated. Further still, the system may provide audible feedback to the user as to the selected electrode configuration and/or voltage output level. For example, in FIG. 6 the audible feedback may be provided by way of speaker 670 coupled to the digital-to-analog converter 606. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

The invention claimed is:

1. A system comprising: a wand comprising a non-conductive outer surface, at least three electrodes disposed on a distal end of the wand, and at least three electrical leads extending from a proximal end of the wand, and electrically coupled, one each, to one of the at least three a controller comprising: a controller connector coupled to the at least three electrical leads; a voltage generator configured to generate voltage of varying amplitude, the voltage generator has an active terminal and a return terminal; and a control circuit coupled between the controller connector and the active and return terminals; the control circuit configured to selectively electrically couple both the active terminal and the return terminal to the at least three electrical leads, such that any of the at least three electrodes are electrically coupled in combination to the voltage generator as an active electrode and as a return electrode.

2. The system of claim 1 wherein the controller further comprises an operator interface device, and wherein the control circuit is configured to selectively electrically couple both the active terminal and the return terminal to the at least three electrical leads based on commands received through the operator interface.

3. The system of claim 1 further comprising a foot pedal assembly operationally coupled to the controller, and wherein the control circuit is configured to selectively electrically couple both the active terminal and the return terminal based on actuation of the foot pedal.

4. The system of claim 1 wherein the wand further comprises an internal passage, and wherein at least one of the at least three electrode resides within the internal passage proximate to the distal end of the wand.

5. The system of claim 1 wherein each of the at least three electrodes of the wand defines a surface area, and at least one of the at least three electrodes has a surface area less than three-quarters the surface area of another of the at least three electrodes.

6. The system of claim 1 wherein a distance between a center of each of the at least three electrodes is constant during deployment and use.

7. The system of claim 1 wherein the control circuit of the controller further comprises:
a first mechanical relay that defines a first coil and first normally-open contact terminals, the first normally-open contact terminals coupled between the active terminal and a first electrode of the at least three electrodes;
a second mechanical relay that defines a second coil and second normally-open contact terminals, the second normally-open contact terminals coupled between the return terminal and the first electrode of the at least three electrodes;
a third mechanical relay that defines a third coil and third normally-open contact terminals, the third normally-open contact terminals coupled between the active terminal and a second electrode of the at least three electrodes;
a fourth mechanical relay that defines a fourth coil and fourth normally-open contact terminals, the fourth normally-open contact terminals coupled between the return terminal and the second electrode of the at least three electrodes;
a fifth mechanical relay that defines a fifth coil and fifth normally-open contact terminals, the fifth normally-open contact terminals coupled between the active terminal and a third electrode of the at least three electrodes; and
a sixth mechanical relay that defines a sixth coil and sixth normally-open contact terminals, the sixth normally-open contact terminals coupled between the return terminal and the third electrode of the at least three electrodes;
wherein the control circuit is configured to selectively electrically couple by selectively powering the first through fifth coils.

8. The system of claim 1 wherein the control circuit of the controller further comprises:
a first means for electrically coupling the active terminal of the voltage generator to a first electrode of the at least three electrical electrodes, and the first means also for electrically isolating the active terminal from the first electrode;
a second means for electrically coupling the return terminal of the voltage generator to the first electrode, and the second means also for electrically isolating the return terminal from the first electrode;
a third means for electrically coupling the active terminal to a second electrode of the at least three electrical electrodes, and the third means also for electrically isolating the active terminal from the second electrode;
a fourth means for electrically coupling the return terminal to the second electrode, and the fourth means also for electrically isolating the return terminal from the second electrode;
a fifth means for electrically coupling the active terminal to a third electrode of the at least three electrical electrodes, and the fifth means also for electrically isolating the active terminal from the third electrode;
a sixth means for electrically coupling the return terminal to the third electrode, and the sixth means also for electrically isolating the return terminal from the third electrode;
wherein the control circuit is configured to selectively electrically couple by selectively activating the first through fifth means for coupling.

9. The system of claim 1 further comprising:
a wand connector coupled to the at least three electrical leads, the wand connector comprising at least three electrical pins, one pin electrically coupled to each electrical lead;
wherein the controller connector and wand connector are configured to couple in only one orientation.

10. The system of claim 9 wherein the wand connector and controller connector further comprise a tab and slot arrangement where the tab and slot are configured to allow the connectors to couple in the only one orientation.

11. The system of claim 10 wherein the tab and slot arrangement is at least one selected from the group consisting of: the tab on the wand connector and the slot on the controller connector; and the tab on the controller connector and the slot on the wand connector.

12. A system comprising:
an electrosurgical wand comprising:
an elongate shaft that defines a proximal end and a distal end;
a connector comprising a plurality of electrical pins;
at least two first electrodes disposed on the distal end of the elongate shaft;
at least two second electrodes disposed on the distal end of the elongate shaft and spaced away from the at least two first electrodes;
wherein each of the electrodes is electrically coupled to one of the plurality of electrical pins via an electrical lead;
wherein each of the at least two first electrodes have a surface area less than three-quarters the surface area of each of the at least two second electrodes;
a control circuit coupled between a first group of connections and a second group of connections, the first group of connections comprising an active terminal and a return terminal of a high frequency voltage generator, and the second group of connections comprising the plurality of electrical pins of the connector, the control circuit configured to switch between a first, second, and third modes;
wherein in the first mode the at least two first electrodes are selectively electrically coupled to the high frequency voltage generator as active electrodes and the at least two second electrodes are selectively electrically coupled to the high frequency voltage generator as return electrodes;
wherein in the second mode the at least two first electrodes are electrically isolated from the high frequency voltage generator and one of the at least two second electrodes is selectively electrically coupled to the high frequency voltage generator as the active electrode and at least another of the at least two second electrodes is selectively electrically coupled to the high frequency voltage generator as the return electrode; and
wherein in the third mode the at least two first electrodes are selectively electrically coupled to the high frequency voltage generator as return electrodes and one of the at least two second electrodes is selectively electrically coupled to the high frequency voltage generator as the active electrode and the other of the at least two second electrodes are electrically isolated from the high frequency voltage generator.

13. The system of claim 12 further comprising an operator interface device operationally coupled to the control circuit, wherein the control circuit is configured to switch between the first, second, and third modes based on commands received through the operator interface device.

14. The system of claim 12 further comprising a foot pedal assembly operationally coupled to the control circuit, wherein the control circuit is configured to switch between the first, second, and third modes based on actuation of the foot pedal assembly.

15. The system of claim 12 wherein the connector and the control circuit are configured to couple in only one orientation.

16. The system of claim 12 wherein each of the electrodes defines a center, and distances between the centers are fixed.

17. The system of claim 12 wherein the control circuit is configured to switch between the first, second, and third modes without de-coupling from the connector.

* * * * *